US007198811B2

(12) United States Patent
Paliyath et al.

(10) Patent No.: US 7,198,811 B2
(45) Date of Patent: *Apr. 3, 2007

(54) COMPOSITIONS FOR THE PRESERVATION OF FRUITS AND VEGETABLES

(75) Inventors: Gopinadhan Paliyath, Waterloo (CA); Dennis P. Murr, Guelph (CA)

(73) Assignee: University of Guelph, Guelph, Ontario (CA)

( * ) Notice: Subject to any disclaimer, the term of this patent is extended or adjusted under 35 U.S.C. 154(b) by 85 days.

This patent is subject to a terminal disclaimer.

(21) Appl. No.: 10/884,864

(22) Filed: Jul. 2, 2004

(65) Prior Publication Data

US 2005/0031744 A1 Feb. 10, 2005

Related U.S. Application Data

(63) Continuation of application No. PCT/CA02/01976, filed on Dec. 20, 2002.

(60) Provisional application No. 60/345,807, filed on Jan. 4, 2002.

(51) Int. Cl.
*A23B 7/14* (2006.01)
(52) U.S. Cl. ............... 426/102; 426/310; 426/541; 426/615
(58) Field of Classification Search ............... 426/615, 426/102, 310, 541
See application file for complete search history.

(56) References Cited

U.S. PATENT DOCUMENTS

| 3,526,520 | A |  | 9/1970 | Kleiman ............... 99/154 |
| 3,764,348 | A | * | 10/1973 | Huxsoll et al. ........ 426/310 |
| 3,865,569 | A | * | 2/1975 | Parups et al. ......... 504/115 |
| 4,988,522 | A |  | 1/1991 | Warren ................. 426/268 |
| 5,126,155 | A |  | 6/1992 | Palta et al. ............ 426/331 |
| 5,198,254 | A |  | 3/1993 | Nisperos-Carriedo et al. .................. 426/102 |
| 5,376,391 | A |  | 12/1994 | Nisperos-Carriedo et al. .................. 426/102 |
| 5,858,436 | A |  | 1/1999 | Bompeix |
| 6,054,160 | A |  | 4/2000 | Gawad et al. ......... 426/270 |
| 6,455,086 | B1 | * | 9/2002 | Trinh et al. ........... 426/321 |
| 6,514,914 | B1 | * | 2/2003 | Paliyath et al. ....... 504/348 |

FOREIGN PATENT DOCUMENTS

| DE | 19917836 A1 | 10/2000 |
| EP | 1106070 A2 | 6/2001 |
| JP | 10262547 | 10/1998 |
| JP | 49123445 | * 5/2006 |
| WO | WO-9105479 | 5/1991 |
| WO | WO-9853707 | 12/1998 |

OTHER PUBLICATIONS

Anet, Edward F., et al., "Superficial Scald, a Functional Disorder of Stored Apples X. Control of Alpha-Farnesene Autoxidation", *J Sci. Food Agr* 25, (1974),293-298.
Barden, Cynthia L., et al., "Accumulation of Antioxidants in Apple Peel as Related to Preharvest Factors and Superficial Scald Susceptibility of the Fruit", *Journal of Amer. Soc Hort. Sci*, 119, (1994),264-269.
Blanpied, G D., et al., "A Survey of the Relationships Among Accumulated Orchard Hours Below 10 Degrees C, Fruit Maturity, and the Incidences of Storage Scald on 'Starkrimson Delicious' Apples", *Can. J. Plant Sci.* 71(1991),605-608.
Harris, W E., et al., "A Fluorescence Method for Study of Cabbage Phospholipase D Activity", *Plant Physiol. Biochem.* 33, (1995),389-398.
Patterson, M E., et al., "The Influence of Oxygen and Carbon Dioxide on the Development of Apple Scald", *Proc. Amer. Soc. Hortic. Sci.* 90, (1962),130-136.
Pierson, C F., et al., "Chemical Injury on Golden Delicious Apples Treated with Diphenylamine", *HortScience* 3, (1968),190.
Pinhero, R G., et al., "Modulation of Phospholipase D and Lipoxygenase Activities During Chilling. Relation to Chilling Tolerance of Maize Seedlings", *Plant Physiol. Biochem* 36, (1998),213-224.
Ghahramani, F , et al., "A Comparison of the Effects of Ethanol and Higher Alcohols for the Control of Superficial Scald in Apples", *Journal of Horticultural Science & Biotechnology*, vol. 74(1), (1999),pp. 87-93.
Lidster, P D., et al., "Application of Flavonoid Glycosides and Phenolic Acids to Suppress Firmness Loss in Apples Malus Domestica", *Biosciences Information Service*, Philadelphia, PA, US—(Abstract), (1986).
Picchioni, G A., et al., "Phospholipid, Galactolipid, and Steryl Lipid Composition of Apple Fruit Cortical Tissue Following Postharvest CaCl-2 Infiltration", *Biosciences Information Service*, Philadelphia, PA, US—(Abstract), (1995).
Wills, R B., et al., "Reduction of Superficial Scald in Apples with Monoterpenes, International Food Information Service (IFIS)", *International Food Information Service (IFIS)*, Franfurt/Main, DE;—(Abstract), (1977).
Zhiqiang, Ju , et al., "Mono-, di-, and tri-acylglycerols and phospholipids from plant oils inhibit scald development in Delicious apples", *International Food Information Service (IFIS)*, Franfurt/Main DE—(Abstract), (2000).

* cited by examiner

*Primary Examiner*—Helen Pratt
(74) *Attorney, Agent, or Firm*—Schwegman, Lundberg, Woessner and Kluth P.A.

(57) ABSTRACT

The invention discloses compositions for the preservation of fruits, vegetables, partially processed products, other produce and followers. The compositions comprise at least one phospholipase D inhibitor, at least one compound comprising an isoprene subunit, at least one component of the flavonoid biosynthetic pathway in a suitable medium. The composition of the present invention may additionally comprise one or more plant growth regulators of the cytokinin type, one or more antioxidants, a membrane stabilizing agent, a surfactant, or any combination thereof. The composition may be applied to produce as a spray, drench, dip, or a vapour and at either the pre-harvest stage or post-harvest stage.

33 Claims, No Drawings

COMPOSITIONS FOR THE PRESERVATION OF FRUITS AND VEGETABLES

RELATED APPLICATIONS

This application is a continuation under 35 U.S.C. 111(a) of International Application No. PCT/CA02/01976 filed Dec. 20, 2002 and published in English as WO 03/059076 A2 on Jul. 24, 2003, which claimed priority from Provisional Application No. 60/345,807 filed Jan. 4, 2002, which applications and publication are incorporated herein by reference.

The invention relates to compositions, and the use of compositions for improving the quality and shelf life of fruits, vegetables, partially processed products, other produce and flowers.

BACKGROUND OF THE INVENTION

Produce production in North America is a multi-billion dollar industry. Consequently, improving and preserving the quality of fruits, vegetables and other types of produce in terms of their colour, taste, flavour and storage-life are of paramount importance to growers, produce-processing companies and the food industry in general. Unfortunately, the time window where most fruits, vegetables and produce exhibit peak quality is relatively narrow, and after this time window, the quality of the produce tends to decrease rapidly.

Superficial scald (or scald) is a physiological disorder that affects certain varieties of apples during or after post-harvest storage, lowering their market value several-fold. Varieties affected include Red Delicious, McIntosh, Cortland, Granny Smith and others. Collectively, these varieties comprise over 60% of the apples produced in Canada and the United States. In addition to affecting apples, superficial scald may also affect certain varieties of pears.

Superficial scald is primarily characterized by damage to the surface of fruit. Often, scald manifests as patchy browning on the surface of the fruit. This symptom can progress to internal damage and contribute to other pathological disorders. Superficial scald development in apples and pears is a form of targeted senescence, where the hypodermal cell layers (3–4 cell layers beneath the cuticle) undergo damage and deterioration. At present, the cause of superficial scald is unknown, but specific plant metabolic pathways have been implicated in its development. Also, environmental conditions such as hot dry weather, nutrient availability, and lack of appropriate chilling conditions during ripening may contribute to the development of superficial scald (Blanpeid et al., 1991; Patterson and Workman 1962).

One theory regarding the mechanism of scald development proposes that the component a-farnescene, present in the superficial cell layers of fruit undergoes peroxidation through an as yet unknown mechanism and the peroxidized products somehow cause tissue damage and browning (Anet and Coggiola, 1974). Supporting the contention that free radicals may be involved in the development of the disorder, application of antioxidants such as a-tocopherol to scald-sensitive fruits can negate the development of superficial scald (Barden and Bramlage, 1994).

Scald development may be inhibited by treating scald-susceptible apples with diphenylamine (DPA) or ethoxyquin. However, some apples such as "Golden Delicious" can develop a blue-grey discoloration on the cheeks and shoulders of the fruit after DPA treatment (Pierson and Schomer, 1968). Further, although DPA and ethoxyquin application inhibit scald development in many varieties of apples, these chemicals may be degraded into compounds which can include potential carcinogens. This has resulted in banning DPA and ethoxyquin application to fruit in several European countries.

Other biochemical pathways have also been implicated in the mechanism of scald development in apples, and the deterioration of produce other than apples. For example, it has been suggested that membrane deterioration during senescence and stress may involve the action of phospholipase D. Phospholipase D (PLD) is a ubiquitous enzyme that catalyses the hydrolysis of membrane phospholipids. However, it has also been proposed that normal maturation and ripening of many types of fruits and vegetables may be due to catabolic breakdown of cellular structures such as the membrane and the cell wall, and that phospholipase D may be directly involved in this process. Also, untimely destruction of cellular integrity of the produce, as often occurs during processing (cutting, wounding, blending, etc) or storage (injury due to chilling) can lead to accelerated destruction of cellular structures, resulting in a loss of quality of the intended product.

There has been much research into compositions that may replace diphenylamine to inhibit scald development in apples, as well as compositions which may be effective in enhancing or extending the food-quality of other produce such as fruits and vegetables.

U.S. Pat. No. 6,054,160 discloses complex compositions and processes for treating fresh-cut apple pieces, as a replacement for sulfite treatment. The composition consists of an antioxidant or reducing component such as cysteine, an osmolite such as sorbitol and a membrane integrity-enhancing agent such as calcium chloride. A chelator such as sodium hexametaphosphate can be added to enhance the affiance of the agent. The compositions are administered by dipping the pieces in an aqueous solution which protect the pieces from deterioration due to increased enzymatic activity, oxidative reactions, water migration and microbes. While the composition may enhance the fresh sensory attributes of freshly cut apples, the composition may not be applied to apples pre-harvest. Furthermore, there is no disclosure as to whether the compositions have any effect on scald, or whether the compositions are effective in enhancing the food quality of other fruits and vegetables.

U.S. Pat. No. 5,858,436 discloses an aqueous treatment composition comprising a polyphenol-type antioxidant alone or in combination with a terpenic compound in an aqueous vehicle for treatment of fruits or vegetables after harvesting. The composition must be heated to a temperature of 40–60° C. and subsequently the fruits or vegetables are brought into contact with the liquid treatment composition at the elevated temperature for a period of less than or equal to 10 minutes. The composition is not suitable for spraying onto fruits and vegetables and the composition must be applied post-harvest.

U.S. Pat. No. 5,376,391 and U.S. Pat. No. 5,198,254 disclose coating compositions which may increase stability of fruits, vegetables or fungi. The compositions comprise at least one polysaccharide polymer, a preservative and an acidulant. The compositions may also include at least one emulsifier, a plasticizer, a resin or rosin, a protein, a firming or sequestering agent, an antioxidant and a plant growth regulator and a chilling injury protectant. It is suggested in the patents that the coatings of the invention may act as a partial barrier to water vapour, oxygen, carbon dioxide and possibly flavour volatiles, thereby causing an alteration in metabolic processes within fruit. No specific metabolic processes or pathways are preferentially inhibited by these compositions, and they may inhibit both beneficial and detrimental metabolic processes within fruits. Moreover, some of the compositions contemplated comprise components which are not normally associated with fruits, vegetables and fungi, or that are normally found in such produce in much lesser quantities. The inclusion of many non-natural components may be undesirable to the consumer. Also, it is unknown whether the disclosed compositions may inhibit superficial scald-development in apples and pears.

U.S. Pat. No. 5,126,155 teaches the use of lysophosphatidylethanolamine for the treatment of pre harvest and post harvest applications.

U.S. Pat. No. 4,988,522 provides compositions useful in the treatment of cut plant parts to improve their quality and storage stability against the effects of oxidation, thermo-oxidation, enzymatic, microbial and metal ion attack. The compositions include an antioxidant, an enzyme inhibitor, an acidulant and a unique metal ion sequestrant which is compatible with the acidulant. Further, the patent teaches that the antioxidant may comprise ascorbic acid and that a chloride ion source may be included. The food preservative compositions disclosed are limited to dips and to treating cut surfaces of edible plant parts. There is no disclosure whether the compositions may be useful for the treatment of superficial scald and other disorders of unprocessed produce.

U.S. Pat. No. 3,526,520 discloses treating and controlling apple storage scald with compostitions comprising diphenylamine, an emulsifier, and an organic solvent. Diphenylamine is a material which may be degraded into potentially toxic compounds. Thus, it is preferable that novel compositions be developed which circumvent the use of diphenylamine to control scald in apples and other fruit.

WO 91/05479 teaches of a preparation for treating apples, pears, and other vegetables to protect them against scald and cold damage. The composition comprises an aqueous solution of sucrose ester(s) and at least one antioxidant selected from natural and synthetic agents including tocopherols, ascorbic acid, esters of gallic acid, vitamin E, butylated hydroxy toluene (BHT), butylated hydroxyanisole (BHA), and 6-O-palmitoyl-L-ascorbic acid. A drawback to the disclosed compositions is that they employ antioxidants which are nonspecific in their functioning as opposed to employing compounds which may directly inhibit specific metabolic pathways that are activated as a result of scald development or cold damage. Furthermore, the application must be done post harvest.

The post-harvest fumigation of apples with ethanol and longer chain alcohols such as hexanol has shown that higher alcohols are less effective than ethanol in controlling superficial scald (Ghahramani et al, 1999).

There is a need in the art for compositions that are generally regarded as safe (GRAS) and that are capable of inhibiting superficial scald in apples and pears and preserving other produce such as, but not limited to fruits, vegetables and portions thereof. Moreover, there is a need in the art for compositions which preserve fruits, vegetables, other produce and flowers, wherein the composition may be applied by spray, drench or by dip. Also, there is a need in the art for compositions which may be used to preserve unprocessed, partially processed or fully processed produce. Further, there is a need in the art for compositions that may be applied either preharvest, or post harvest, for the preservation of fruits, vegetables, other produce and flowers, wherein the compositions comprise components which inhibit specific metabolic pathways and thus provide both targeted and preventative damage control.

It is an object of the present invention to overcome drawbacks in the prior art.

The above object is met by a combination of the features of the main claims. The sub claims disclose further advantageous embodiments of the invention.

SUMMARY OF THE INVENTION

The invention relates to compositions, and the use of compositions for improving the quality and shelf life of fruits, vegetables, partially processed products, other produce and flowers.

According to the present invention, there is provided, a composition for the preservation of produce comprising;
  a) at least one phospholipase D inhibitor;
  b) at least one compound comprising an isoprene subunit; and
  c) at least one component of the flavonoid biosynthetic pathway, in a suitable medium.

The at least one phospholipase D inhibitor may be selected from the group consisting of hexanal, hexenol, hexenal, geraniol, or a combination thereof; the at least one compound comprising an isoprene subunit may be selected from the group consisting of geraniol, geranylacetate, neral, nerol, citronellal, citronellol, or a combination thereof, and the at least one component of the flavonoid biosynthetic pathway may be selected from the group consisting of para-coumaric acid, trans-cinnamic acid, caffeic acid or a combination thereof. Optionally, the composition as defined above may further comprising at least one plant growth regulator, wherein the growth regulator is a cytokinin.

The present invention also pertains to the composition as defined above, further comprising an antioxidant, a membrane/cell wall stabilizing agent, a surfactant, or a combination thereof The antioxidant may be selected from the group consisting of ascorbic acid, ascorbate palmitate, α-tocopherol, α-tocopherol acetate, and a combination thereof, and the membrane/cell wall stabilizing agent is calcium chloride.

The present invention provides a method for preserving produce comprising, applying an effective amount of a composition comprising, at least one phospholipase D inhibitor, at least one compound comprising an isoprene subunit, and at least one component of the flavonoid biosynthetic pathway, in a suitable medium. The composition may additionally comprise an antioxidant, a membrane stabilizing agent, a surfactant, or a combination thereof.

The present invention also pertains to the above method, wherein the step of applying comprises spraying, dipping, or storage in a medium comprising the composition. Further, the present invention relates to a matrix coated or impregnated with the composition as just defined.

The present invention also provides an antioxidant composition for the preservation of produce and flowers comprising at least one antioxidant selected from the group consisting of ascorbic acid, ascorbyl palmitate, α-tocopherol, α-tocopherol acetate, and a combination thereof, in a suitable medium. The composition as just defined may also comprise a membrane/cell wall stabilizing agent.

The present invention also embraces a method for preventing sunscald or superficial scald in produce, or improving the shelf life of flowers comprising applying an effective amount of the antioxidant composition as just defined to the produce.

The present invention pertains to a method for enhancing:
  anthocyanin level in fruit;

firmness, sweetness, shelf life, fruit quality or a combination thereof in fruit levels of proteins and isoflavonoids in soybean, sugar level of beets or sugar cane, or shelf life of cut flowers, comprising, applying an effective amount of the antioxidant composition as just defined to the fruit, soybean, beets, sugarcane, or cut flowers as the case may be.

The present invention is also related to an enzyme activity modulator composition for the preservation of produce comprising geraniol, geranyl acetate, hexanal and coumaric acid in a suitable medium.

The present invention also provides a method for preserving produce comprising, applying an effective amount of the enzyme activity modulator composition as just defined to the produce.

According to the present invention, there is provided a composition for the preservation of produce, the composition comprising at least one phospholipase D inhibitor, one or more than one compound comprising an isoprene subunit, one or more than one component of the flavonoid biosynthetic pathway, in a suitable medium. The composition of the present invention may additionally comprise one or more than one plant growth regulator, one or more than one antioxidant, a membrane stabilizing agent, a surfactant, or any combination thereof.

Also according to the present invention is the use of the composition of the present invention as defined above for the preservation of produce such as fruits and vegetables. In addition, the produce may be processed, unprocessed or partially processed produce, and for enhancing shelf life of cut flowers.

Also according to the present invention, there is provided a method for the preservation of produce comprising; applying an effective amount of a composition to produce, wherein the composition comprises at least one phospholipase D inhibitor, at least one compound comprising an isoprene subunit at least one component of the flavonoid biosynthetic pathway and at least one plant growth regulator in a suitable medium. The composition of the present invention may additionally comprise one or more antioxidants, a membrane stabilizing agent, a surfactant, or any combination thereof. Further, an effective amount of the composition may be applied by spraying, drenching, dipping or evaporation.

This summary does not necessarily describe all necessary features of the invention but that the invention may also reside in a sub-combination of the described features.

DESCRIPTION OF PREFERRED EMBODIMENT

The invention relates to compositions, and the use of compositions for improving the quality and shelf life of fruits, vegetables, partially processed products, and other produce.

The following description is of a preferred embodiment by way of example only and without limitation to the combination of features necessary for carrying the invention into effect.

The composition of the present invention may be used to negate the development of, but is not limited to, superficial scald, sunscald, maintain or increase anthocyanin levels, and inhibit other physiological disorders that may develop during the preharvest period or during post harvest storage. Also, the compositions of the present invention may enhance, maintain, or increase the color, firmness, sweetness, flavour, shelf life, chilling tolerance, weight, level of nutraceuticals, and level of phytochemicals of processed, unprocessed or partially processed produce. The application of one or more of the formulations described herein may be made either preharvest, while the product is still attached to a plant or tree, or post harvest.

Unprocessed produce refers to harvested or unharvested fruits, vegetables or other produce which are not substantially different in appearance from their natural state. For example, apples harvested from trees or lettuce harvested from the ground are representative examples of unprocessed produce. Partially processed produce refers to produce which has been subjected to at least one mechanical, chemical or physical process which alters the natural state or appearance of the produce. Representative examples of partially processed produce include, but are not limited to produce which is cut, chopped, peeled, diced, mashed, squeezed, partially processed, etc. Fully processed produce refers to produce which have been subjected to multiple mechanical, chemical or physical processes.

According to the present invention there is provided a composition for the preservation of produce comprising at least one phospholipase D inhibitor, at least one compound comprising an isoprene subunit, and at least one component of the flavonoid biosynthetic pathway in a suitable medium. Optionally, the composition may also include at least one plant growth regulator of the cytokinin type, an antioxidant, a membrane stabilizing agent, a surfactant, or a combination thereof.

By the term "preservation" it is meant the enhancement, maintenance or extension of the lifetime of the organoleptic qualities of the produce, for example, but not limited to color, sweetness, taste, flavor, storage-lifetime, nutritional quality or combinations thereof. These qualities can be determined using standard taste tests or visual inspection as would be known to a person of skill in the art.

By the term "phospholipase D inhibitor", it is meant a compound which is capable of inhibiting the activity of phospholipase D. Preferably the phospholipase inhibitor exhibits inhibitory activity towards phospholipase D at micromolar or more dilute concentrations and reduces phospholipase D activity by at least about 10% compared to the phospholipase D activity observed in the absence of the phospholipase D inhibitor. There are many assays known in the art which may be used to measure the activity of phospholipase D, for example but not limited to an assay described by Pinhero et al., (1998; which is herein incorporated by reference). Without wishing to be bound by theory, phospholipase D may be involved in the development of superficial scald (a form of targeted senescence, where the hypodermal cell layers undergo damage and deterioration), and other senescent processes.

Phospholipase D inhibitors include, but are not limited to hexenal, hexanal, hexenol, hexanol, and combinations thereof. Someone of skill in the art will note that the fore-mentioned phospholipase D inhibitors comprise compounds having six carbon atoms (C6 compounds). The present invention also contemplates phospholipase D inhibitors having greater than six carbon atoms, for example, but not limited to geraniol, or less than six carbon atoms. Preferably, C6 components are employed in the composition of the present invention, as these components are naturally present in fruits and vegetables as flavor components. Other phopholipase D inhibitors may be used, for example but not limited to lysophosphatidylethanolamine (U.S. Pat. No. 5,126,155, which is incorporated herein by reference). A non-limiting example of phospholipase D inhibitor is hexanal.

Without wishing to be bound by theory, hexanal, may be reduced to hexanol through the action of alcohol dehydrogenase-mediated reduction. The alcohols may be subject to esterification by alcohol:acyl CoA acyl transferase, giving rise to ester volatiles, that are integral components of flavour in apples and pears. Esters containing C6 components (hexanol, hexanoic acid) are common in apples. Scald-developing sides of apples produce lesser amounts of these esters than the normal sides (Paliyath et. al. 1997, Food Res. International, 30:95–103). Thus, supplying hexanal through a composition of the present invention may also have a protective effect.

The compositions of the present invention comprise at least one compound comprising an isoprene unit (1,3 butadiene) of the formula:

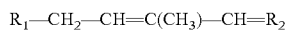

$$R_1\text{—}CH_2\text{—}CH\text{=}C(CH_3)\text{—}CH\text{=}R_2$$

where $R_1$ and $R_2$ may be any suitable chemical substituents. The compound comprising an isoprene subunit may comprise less than about 20 carbons, or less than about 15 carbons. In a non-limiting example, the compound comprising an isoprene subunit comprises less than or about 10 carbon atoms. However, mixtures of compounds comprising isoprene subunits with differing numbers of carbon atoms are contemplated by the present invention. Compounds comprising isoprene units include, but are not limited to, terpenic or monoterpenic compounds for example, but not wishing to be limiting, monoterpenic compounds with a C10 skeleton, for example, geraniol, geranyl acetate, neral, nerol, citronellal, and citronellol.

By the term "component of the flavonoid biosynthetic pathway" it is meant any compound, intermediate or derivative thereof which may be used in the biosynthesis of flavonoids. Components of the flavonoid biosynthetic pathway include but are not limited to coumaric acid, para-coumaric acid, trans-cinnamic acid, caffeic acid, phenylalanine, acetyl CoA and malonyl CoA. The component of the flavonoid biosynthetic pathway may be para-coumaric acid, trans-cinnamic acid, caffeic acid, or a combination thereof For example, but not wishing to be limiting, the component of the flavonoid biosynthetic pathway is para-coumaric acid.

Without wishing to be bound by theory, by adding one or more components of the flavonoid biosynthetic pathway, this may enhance or prolong organoleptic qualities of produce by promoting the biosynthesis of flavonoids within the treated fruit or vegetable, which may in turn lead to the biosynthesis of anthocyanins. For example coumaric acid may be converted to coumaryl CoA by fruit and the combination of coumaryl CoA with 3 malonyl CoA gives rise to chalcone, the basic flavonoid skeleton. Biosynthesis of flavonoids increases during ripening in fruits, and this may lead to the biosynthesis of anthocyanins which provide colour to the fruit.

The compositions of the present invention may also comprise a "plant growth regulator" selected from the group consisting cytokinins, cytokinin-type compounds, or compounds that exhibit a similar action to cytokinins. Preferably, the plant growth regulator has the ability to rejuvenate senescing tissues. Plant growth regulators may further include, but are not limited to, benzyl adenine, kinetin, isopentenyl-adenine, zeatin, polyamines, and polycationic amino acids, for example polylysine.

Without wishing to be bound by theory, one or more plant growth regulators, for example, but not limited to cytokinins, may enhance antioxidant function by inducing the biosynthesis of peroxidases which are important in the detoxification of reactive oxygen species. Superficial scald development has been associated with an enhanced level of active oxygen generation and a deficiency in antioxidant enzyme function. Without wishing to be bound by theory, benzyl adenine, polyamines or polycationic amino acids may enhance peroxidase levels within the epidermal and hypodermal cell layers of scald-susceptible apple cultivars (e.g. McIntosh, Red Delicious, Cortland, etc.) making these cultivars more resistant to the development of superficial scald.

By the term "suitable medium" it is meant a solvent which is capable of dispersing, dissolving, or dispersing and dissolving, the components of the composition. A suitable medium may include, but is not limited to ethanol, or a combination of ethanol and water. As someone of skill in the art will understand a suitable medium must be non-damaging at the levels to be applied to the produce. Furthermore, the medium must be non-toxic at the concentration that would be ingested after applying an effective amount of the composition of the present invention to produce, and subsequently consuming the composition-coated produce.

The compositions of the present invention may also comprise an antioxidant such as, but not limited to, ascorbic acid, ascorbyl palmitate, α-tocopherol, α-tocopheryl acetate, α-tocopherol acetate, or combinations thereof.

The compositions of the present invention may also comprise a membrane stabilizing agent. By the term "membrane/cell wall stabilizing agent" it is meant a compound which enhances cell membrane, or cell wall integrity. Membrane/cell wall stabilizing agents include, but are not limited to polyamines, such as spermine, spermidine and the like, polymers such as, but not limited to chitin, and chitosan, and salts such as, but not limited to calcium chloride. A preferred membrane/cell wall stabilizing agent is calcium chloride, however, other compounds may be used if readily available, or if available at reasonable cost.

Without wishing to be bound by theory, membrane stabilizing agents such as calcium chloride may act as an important regulatory component of several biochemical processes in the cell, and enhance antioxidant enzyme system function and cell wall integrity.

The composition of the present invention may also comprise one or more surfactants. By the term "surfactant" it is meant a compound which comprises both a relatively polar portion and a relatively apolar portion and which is capable reducing the surface tension of water. Surfactants include, but are not limited to food grade surfactants and detergents known by those skilled in the art, including AGB 2045, TWEEN® 20 and TWEEN® 40. Preferably, the surfactant is a food grade surfactant.

To preserve fruits, vegetables, other produce and flowers, the compositions of the present invention are applied in effective amounts to the fruit, vegetable, produce or flowers. This effective amount may be readily determined following the procedures outlined herein.

According to an aspect of the present invention, there is provided a composition comprising:

at least one phospholipase D inhibitor, one or more compounds comprising an isoprene subunit, one or more compounds of the flavonoid biosynthetic pathway, one or more antioxidant compounds.

Such a composition, either alone, or in combination with other components is effective in reducing or eliminating scald, reducing softening, maintaining colour, and maintaining or increasing the soluble solid content in fruit (see Tables 1-3C and 4-12B).

According to an aspect of the present invention, there is provided an enzyme activity modifier (EAM) composition comprising:
at least one phospholipase D inhibitor,
one or more compounds comprising an isoprene subunit, and
one or more compounds of the flavonoid biosynthetic pathway.

Such a composition, either alone, or in combination with other components is effective in reducing or eliminating scald, reducing softening and maintaining or increasing the soluble solid content in fruit (see Tables 3D and 9 in Examples 3 and 4, respectively). Furthermore, components of the EAM formulation are active in maintaining firmness or increasing soluble solids content of fruit (see Table 9, Example 4)

The EAM formulation, or a component thereof, may be prepared as a stock solution comprising:
at least one phospholipase D inhibitor, from about 5 mM to about 500 mM, preferably from about 40 mM to about 100 mM;
one or more compounds comprising an isoprene subunit, from about 5 mM to about 500 mM, preferably from about 50 mM to about 100 mM; and
one or more compounds of the flavonoid biosynthetic pathway, from about 5 mM to about 500 mM, preferably from about 30 mM to about 100 mM, and diluted before use.

Compounds which may be optionally included in the compositions of the present invention include:
at least one plant growth regulator, from about 1 mM to about 50 mM, preferably from about 4 mM to about 10 mM.
one or more antioxidants, from about 5 mM to about 500 mM, preferably from about 50 mM to about 100 mM;
one or more membrane stabilizing agents from about 0.5 mM to about 100 mM, preferably from about 10 mM to about 70 mM in the final solution; and
a surfactant from about 0.001% to about 0.2%, preferably from 0.01% to about 0.1% (w/w) in the final solution.

A solution that may be applied to produce may be obtained by diluting the stock solution in water by about 100 to about 1,000 fold.

Also provided within the present invention is an antioxidant (AOX) composition comprising ascorbate, ascorbate palmitate, α-tocopherol and α-tocopherol acetate. This composition is also effective in reducing scald and maintaining firmness in fruit (see Table 3E, Example 3), as well as in increasing the shelf life of cut flowers (see Table 13, Example 8). The AOX composition contains from about 5 mM to about 500 mM antioxidants an amount therebetween, for example but not limited to from about 50 mM to about 100 mM, or an amount there between.

Compounds which may be optionally included in the compositions of the present invention include:
at least one plant growth regulator, from about 1 mM to about 50 mM, preferably from about 4 mM to about 10 mM.
one or more membrane stabilizing -agents from about 0.5 mM to about 100 mM, preferably from about 10 mM to about 70 mM in the final solution; and
a surfactant from about 0.001% to about 0.2%, preferably from 0.01% to about 0.1% (w/w) in the final solution.

A solution that may be applied to produce may be obtained by diluting the stock solution in water by about 100 to about 1,000 fold.

The present invention also contemplates compositions which may comprise two or more phospholipase D inhibitors, compounds comprising an isoprene subunit, components of the flavonoid biosynthetic pathway, and optionally two (or more) plant growth regulators, antioxidants, membrane stabilizing agents, surfactants, or combinations thereof The components of each group may differ in hydrophobicity such that one of the components may partition preferentially into a membrane whereas the other component may remain in a more hydrophilic environment. Without wishing to be bound by theory, the more hydrophobic component may provide protection against detrimental processes which originate in a membrane compartment, while the more hydrophilic component may provide protection against detrimental processes which originate in a hydrophilic compartment. For example, but not wishing to be limiting, the composition of the present invention may comprise geranyl acetate and geraniol as compounds comprising an isoprene unit. Without wishing to be bound by theory, geranyl acetate, which is more lipophilic than geraniol. Once inside the cell, endogenous esterase action may liberate geraniol from geranyl acetate.

The compositions of the present invention may also comprise one or more antioxidants such as, but not limited to ascorbic acid, ascorbyl palmitate, α-tocopherol, α-tocopheryl acetate, α-tocopherol acetate, or combinations thereof. Antioxidants reduce the level of active oxygen species which may be a major contributor to scald development and spoilage of produce. Without wishing to be bound by theory, ascorbyl palmitate, tocopheryl acetate or α-tocopherol acetate are more hydrophobic than ascorbic acid and tocopherol, respectively and thus these more hydrophobic components may provide better protection within cell membranes. Reduction of the level of active oxygen species in produce such as, but not limited to fruits, vegetables and flowers may enhance and extend their shelf life and maintain their nutritional quality.

The present invention also contemplates compositions wherein the individual components may have multiple functions. For example, but not wishing to be limiting, geraniol, a higher analog of hexanol, is a compound comprising an isoprene subunit, and this compound may also be capable of inhibiting phospholipase D activity.

The compositions of the present invention may be applied to fruits, vegetables and flowers pre-harvest, post-harvest, or both. Further, application of the composition of the present invention may be performed using any methods known in the art. For example, but not wishing to be limiting, the composition of the present invention may be applied to produce as a spray, drench, dip, a vapor, or any combination thereof. Spray treatment may be preferable in instances such as pre-harvest application (where dipping or drenching may not be feasible). Further, spray treatment may reduce labor associated with dip treatments, for example, but not limited to storage operation costs and it may also eliminate waste disposal since exact quantities of the composition can be prepared and applied to produce. Vapor treatment may be used in post harvest applications, and could involve adding the composition as described herein to any suitable matrix, for example, but not limited to an impregnated papers, cloth or synthetic polymer sheet, packaging medium materials, and the impregnated matrix placed in the vicinity of the harvested produce. Compositions of the present invention, for example but not limited to AOX compsotions, applied to a matrix exhibit preservative activity (e.g. for broccoli florets: protein content at day 0: 3.03 mg/100 mg FW, and after 12 days in the control: 1.78 mg/100 mg FW; v. AOX treatment after 12 days: 2.39 mg/100 mg FW).

Therefore, the present invention also provides a composition comprising a matrix material coated or impregnated with at least one phospholipase D inhibitor, one or more compounds comprising an isoprene subunit, one or more compounds of the flavonoid biosynthetic pathway, and optionally one or more antioxidant compounds, a plant growth regulatory, one or more membrane stabilizing agents, a surfactant, or a combination thereof.

The compositions of the present invention circumvent concerns associated with diphenylamine (DPA) disposal. For example, DPA cannot be discharged into water streams, but must be diluted and sprayed onto the orchard floor.

It is also contemplated that the compositions of the present invention may be used for the storage of unprocessed, partially processed, or fully processed produce. Examples of such embodiment include, but are not limited to canned or pickled products.

Application of the composition of the present invention to produce may enhance color development, for example, but not limited to, as in apples and peaches. Thus, the composition of the present invention may be applied to produce to potentially enhance the sweetness, colour (anthocyanins), flavour and keeping quality of fruits. Further, the present invention contemplates compositions which may be applied to grapes to enhance or maintain their nutraceutical quality, as well as wines made from them.

The compositions of the present invention may also be used on many types of produce, for example, but not limited to monocots, dicots, legumes and fungi. Specific example include, but are not limited to apples, pears, cherries, peaches, nectarines, grapes, apricots, plums, prunes, soybeans, citrus fruits such as, but not limited to orange, grapefruits and tangerines, celery, carrots, broccoli, cabbage, brussel sprouts, spinach and other leafy vegetables, berry crops such as but not limited to blueberries, cranberries, currants, lettuce, cucumbers, tomatoes, peppers, herbs, and bananas.

The composition of the present invention may be applied as a preharvest spray to soybeans to potentially enhance the levels of proteins and isoflavonoids, to beets and sugar cane to enhance sugar levels, or to cereal crops to enhance the level of protein in the seeds. Further, flowers may be sprayed or dipped into the composition of the present invention. In such an embodiment, the compositions may enhance the longevity and extend the shelf-life of the flowers.

The above description is not intended to limit the claimed invention in any manner, furthermore, the discussed combination of features might not be absolutely necessary for the inventive solution.

All references are herein incorporated by reference.

The present invention will be further illustrated in the following examples. However, it is to be understood that these examples are for illustrative purposes only, and should not be used to limit the scope of the present invention in any manner.

EXAMPLE 1

A Representative Example of a Composition for the Preservation of Fruits, Vegetables and other Produce An example of stock solutions that may be used for the treatment of produce is provided below, however it is to be understood that these solutions are provided as examples only and are not to be considered limiting in any manner.

Stock Solution A Comprises:

83 mM Hexanal 57 mM Geraniol 44 mM Geranyl Acetate 30 mM Coumaric acid 8.8 mM Benzyl Adenine Stock Solution B Comprises:

56 mM L-Ascorbic acid 24 mM Ascorbyl palmitate 15 mM α-tocopherol 2 mM α-tocopherol acetate Solution C comprises $CaCl_2$, at a final concentration of 1% in the solution applied to fruits, vegetables, or produce.

Solution A and Solution B are made in absolute ethanol.

5–10 mL of Solution A is mixed with 5–10 mL of Solution B, and the resulting solution is diluted in water to 1 L. Optionally, calcium chloride (1% w/v) and a surfactant (0.01% w/v) may be included in the final 1 L solution. The formulation may be applied to processed or unprocessed fruits, vegetables, produce or flowers as a preharvest or postharvest spray or dip. Alternatively, the formulation may be added to a liquid which surrounds vegetables, produce or flowers, applied using an atomizer, or applied to a matrix for use as a vapor treatment of produce.

EXAMPLE 2

Effect of Preservative Compositions of the Present Invention on Scald Development in Apples A) Effects of Spraying Compositions of the Present Invention on Scald Development in Apples The effect of the compositions of the current invention on the scald development is examined. About 4 bushels of apples are divided into about 4 sets of about 50–60 apples each. One set of apples is dipped into a control solution of water comprising 10 mL/L ethanol and 1 mL/L detergent (ABG 7045; or Sylgard 309, Dow Corning) while another set is dipped in a composition of the present invention prepared according to Example 1 comprising Solutions A, B and C. Apples are allowed to dry and are subsequently transferred to air (0° C.) or a controlled atmosphere comprising 3% $O_2$, 2.5% $CO_2$ at 0° C. Air stored apples are examined after about 18–19 weeks, while controlled atmosphere-stored apples are brought out after about 20–21 weeks. Apples are evaluated for scald after about one week after storing at room temperature. Apples that show any discolouration (browning) are considered scalded apples. The percentage scald represents the number of apples exhibiting scald divided by the total number of apples in the sample multiplied by 100%. In Trials 1 and 3, apples are brought to room temperature after storage. In Trials 2 and 4, apples are evaluated after 1 week of storage at room temperature. The results are illustrated in Table 1.

TABLE 1

Effect of Compositions of the Present Invention
on Scald Development in McIntosh Apples Air Stored Apples

| Experimental Set | % scald (±SEM)[a] Trial 1 | % scald (±SEM) Trial 2 |
|---|---|---|
| Control | 9.8 ± 3.2 | 43.0 ± 6.0 |
| +Composition | 1.5 ± 1.5 | 13.0 ± 2.8 |
| Experimental Set | % scald (±SEM) Trial 3 | % scald (±SEM) Trial 4 |
| Control | 0 | 34.5 ± 4.1 |
| +Composition | 0 | 11.2 ± 1.7 |

Controlled-Atmosphere stored apples

| Experimental Set | % scald (±SEM) Trial 1 | % scald (±SEM) Trial 2 |
|---|---|---|
| Control | 1.2 ± 1.2 | 35.0 ± 2.0 |
| +Composition | 1.2 ± 1.2 | 8.7 ± 1.2 |
| Experimental Set | % scald (±SEM) Trial 3 | % scald (±SEM) Trial 4 |
| Control | 8.7 ± 1.2 | 23.8 ± 4.2 |
| +Composition | 2.5 ± 1.4 | 6.2 ± 1.2 |

[a]SEM: standard error of the mean. Trials 1 and 3 represent data obtained when apples are brought to room temperature. Trials 2 and 4 represent data obtained when apples are evaluated after one week at room temperature.

As shown in table 1, the composition of the present invention reduces scald development in apples. Further, a reduction in scald development is observed regardless of whether the apples are stored in air or under controlled atmosphere conditions.

B) Effects of Spraying Compositions of the Present Invention on Scald Development in Apples Two trees are used as controls and two trees are used for treatment using a composition prepared according to Example 1 comprising solutions A, B and C. About two weeks after spraying with the composition of the present invention, about half of the apples on each tree were harvested (H1) and the trees were sprayed again. The remainder of the apples were harvested about 1 week later (H2). Harvested apples are stored in air or under a controlled atmosphere (3% $O_2$, 2.5% $CO_2$, 0° C.) for about 4 weeks. After storage, apples are evaluated for scald. Scald was evaluated as described in Example 1.

TABLE 2

Effects of Spraying Compositions of the Present Invention
on Scald Development in McIntosh Apples Air Stored Apples

| Experimental Set | % scald (±SEM) Trial 1 | % scald (±SEM) Trial 2 |
|---|---|---|
| H1 Control | 32.0 ± 4.0 | 65.0 ± 3.0 |
| H1 +Composition | 11.0 ± 1.7 | — |
| Experimental Set | % scald (±SEM) Trial 3 | % scald (±SEM) Trial 4 |
| H2 Control | 8.0 ± 1.7 | 71.0 ± 1.7 |
| H2 +Composition | 6.0 ± 2.6 | 19 |

Controlled-Atmosphere Stored Apples

| Experimental Set | % scald (±SEM) Trial 1 | % scald (±SEM) Trial 2 |
|---|---|---|
| H1 Control | 7.5 ± 4.0 | 51.0 ± 5.5 |
| H1 +Composition | 2.5 ± 1.4 | 25.0 ± 2.8 |
| Experimental Set | % scald (±SEM) Trial 1 | % scald (+SEM) Trial 2 |
| H2 Control | 5.0 ± 2.0 | 54.0 + 4.0 |
| H2 +Composition | 2.5 ± 1.4 | 17.5 |

As shown in table 2, the compositions of the present invention may be sprayed onto apples to reduce the development of scald. Further, a reduction in scald development is observed regardless of whether the apples are stored in air or under controlled atmosphere conditions.

Referring now to Table 3A, there is shown the effect of the composition prepared according to Example 1 of the present invention on the development of scald in various apple varieties. The composition of the present invention is applied as described above.

TABLE 3A

The Effect of Compositions of the Present Invention on
the Development of Scald in Various Apple Varieties.

| Apple Type | Storage Conditions | % scald ± SEM Control | % scald ± SEM +Composition |
|---|---|---|---|
| Morspur McIntosh | Air, day 0 | 3.75 ± 2.39 | 1.25 ± 1.25 |
| | Air, day 7 | 52.5 ± 4.30 | 1.50 ± 2.04 |
| | CA[b], day 0 | 3.75 ± 1.25 | 0 |
| | CA day 7 | 20.00 ± 2.04 | 3.75 ± 1.25 |
| Marshall McIntosh | Air, day 0 | 8.75 ± 3.70 | 1.25 ± 1.25 |
| | Air, day 7 | 58.75 ± 2.40 | 27.50 ± 2.40 |
| | CA, day 0 | 42.5 ± 3.22 | 11.25 ± 1.25 |
| | CA day 7 | 81.25 ± 4.27 | 51.25 ± 3.14 |
| Cortland | Air, day 0 | 16.75 ± 3.60 | 4.37 ± 2.95 |
| | Air, day 7 | 45.55 ± 3.60 | 23:52 ± 6.28 |
| Red Delicious | Air, day 0 | 0 | 0 |
| | Air, day 7 | 39.00 ± 3.75 | 16.00 ± 2.40 |
| Empire | Air, day 0 | 0 | 0 |
| | Air, day 7 | 1.25 + 1.25 | 1.25 ± 1.25 |

[b]CA refers to controlled atmosphere as described in Example 2.

The compositions of the present invention are useful for inhibiting scald development in many varieties of apples. As shown in table 3A, compositions of the present invention reduce scald development in varieties of apples such as but not limited to Morspur McIntosh, Marshall McIntosh, Cortland, and Red Delicious. The effect of the composition of the present invention on Empire apples, which are resistant to scald is used as a control.

The results suggest that the formulation of the present invention does not damage fruit. Further, a reduction in scald development is observed in most apples regardless of whether the apples are stored in air or under controlled atmosphere conditions.

C) Effect of the Composition of the Present Invention on Superficial Scald Development in Apples.

Apples were harvested at optimum maturity as indicated by a starch test as known to those skilled in the art. Apples (50–60) were dipped in the formulation of Example 1 (diluted at 10 ml/liter) for a period of 5 min. and allowed to dry at room temperature. The dipped apples, along with untreated controls were stored in air at 0° C. for a period of six months before analysis. Apples were brought to room temperature, twenty representative apples were picked at random from each replicate and left at room temperature for a period of one week prior to estimating scald. Results are present in Table 3B.

TABLE 3B

The Effect of Compositions of the Present Invention on the Development of Scald in Various Apple Varieties.

| Orchard | Control | | +Composition | |
|---|---|---|---|---|
| | | % Scald Development | | |
| Red Delicious Apples | | | | |
| Denbock | 60 | 60 | 0 | 5 |
| Simcoe | 70 | 70 | 15 | 20 |
| Arthur (1) | 50 | 65 | 5 | 5 |
| Arthur (2) | 40 | 70 | 5 | 10 |
| McIntosh Apples | | | | |
| Denbock | 40 | 30 | 5 | 0 |
| | — | — | 15 | 5 |
| Cortland Apples* | | | | |
| St. Jean | 92 | — | 22 | — |

*stored in controlled atmosphere: 3% $O_2$, 2.5% $CO_2$

D) Effect of the Composition, and Components of the Composition, of the Present Invention on Superficial Scald Development and Softening in Apples.

The effects of antioxidant formulation of the present invention, and subgroups of its chemical components on post harvest qualities of Cortland apples were investigated.

Apples were dipped in:
1) the whole formulation (prepared as outline in Example 1), these results are shown in Table 3C;
2) a subgroup that comprises enzyme activity modulators (EAM), these results are shown in Table 3D;
3) another subgroup containing antioxidants (AOX), these results presented in Table 3E;
4) 1500 ppm of diphenylamine (DPA; the present method of controlling scald, results in each of Tables 3C–3E); or
5) left untreated, (control, results presented in each of Tables 3C–3E).

The effect of the duration of dip treatment of Cortland apples using the antioxidant formulation (Example 1, Solution B) is presented in Table 3C. Ten ml of the formulation of was diluted to a liter. The solution also contained 1% calcium chloride (w/v final) and 0.1% (v/v final) surfactant. Two bushels of apples were dipped in 40 liters of the formulation from 10 seconds, up to 5 minutes as indicated in Table 3C, allowed to dry overnight and stored under controlled atmosphere (2.5% oxygen, 3% carbon dioxide, 3° C.) in a commercial storage operation for 9 months before evaluation. Twenty randomly selected apples from each of the treatments were removed and kept at room temperature for a week before evaluations were conducted.

TABLE 3C

Thee effect of Composition of the Present Invention (Example 1) on Scald development in Cortland apples. The number of apples showing scald or softening is expressed as a percentage of the total number of apples evaluated. The values are the mean from two independent evaluations.

| Duration of Treatment | Superficial scald % | Softening % |
|---|---|---|
| Untreated Control | 67.5 | 65 |
| 10 seconds | 12.5 | 60 |
| 1 minute | 27.5 | 57.5 |
| 2.5 minute | 7.5 | 17.5 |
| 5 minute | 17.5 | 50 |
| DPA-treated (1 minute, 1500 ppm) | 35 | 25 |

The results in Table 3C demonstrates that use of the entire formulation reduces both superficial scald and softening in fruit. Furthermore, the composition of Example 1 is as, or more, effective than DPA treatment.

The effect of a modified formulation of Example 1, comprising enzyme activity modulators (EAM-formulation), on superficial scald development and softening is presented in Table 3D. The modified formulation comprises hexanal, geraniol, geranyl acetate and coumaric acid at the concentration originally present in the full formulation. No benzyl adenine L-ascorbic acid, ascorbyl palmitate, α-tocopherol, α-tocopherol acetate is present in the EAM formulation.

Ten ml of the concentrate of the EAM formulation was diluted to one liter to form the final solution. The solution also contained calcium chloride (1% w/v, final) and surfactant (0.1% v/v final). Two bushels of apples were dipped in 40 liters of solution for each time period and subjected to controlled atmosphere storage as defined above. Apples were brought out after 9 months of storage. Twenty apples from each treatment were picked randomly from two independent sets, and left at room temperature for one week before evaluating for scald and softening.

TABLE 3D

The effect of a EAM composition of the present invention on scald development in Cortland apples. The number of apples showing scald or softening is expressed as a percentage of the total number of apples evaluated. The values are the mean from two independent evaluations.

| Duration of Treatment | Superficial scald % | Softening % |
|---|---|---|
| Untreated Control | 67.5 | 65 |
| 10 seconds | 25 | 40 |
| 1 minute | 32.5 | 42.5 |
| 2.5 minute | 55 | 7.5 |
| 5 minute | 42.5 | 17.5 |
| DPA-treated (1 minute, 1500 ppm) | 35 | 25 |

The results in Table 3D demonstrates that use of the EAM formulation is effective in reducing superficial scald. However, this treatment appears to reduce the softening considerably, potentially due to a reduction of membrane phospholipid degradation.

The effect of a second modified formulation of the present invention, comprising antioxidants (AOX formulation) on superficial scald development and softening is presented in Table 3E. The components of the AOX formulation include ascorbate, ascorbate palmitate, α-tocopherol and α-tocopheryl acetated (or α-tocopherol acetate) at the concentration originally present in the full formulation. No hexanal, geraniol, geranyl acetate, coumaric acid or benzyl adenine were present in the AOX formualtion.

Ten ml of the concentrate of the AOX formulation was diluted to one liter to form the final solution. The solution also contained calcium chloride (1% w/v final) and surfactant (0.1% v/v, final). Two bushels of apples were dipped in 40 liters of solution for each time period and subjected to controlled atmosphere storage as defined above. Apples were brought out after 9 months of storage. Twenty apples, from each treatment were picked randomly from two independent sets, and left at room temperature for one week before evaluating for scald and softening. The results are presented in Table 3E.

TABLE 3E

The effect of an AOX composition of the present invention on scald development in Cortland apples. The number of apples showing scald or softening is expressed as a percentage of the total number of apples evaluated. The values are the mean from two independent evaluations.

| Duration of Treatment | Superficial scald % | Softening % |
|---|---|---|
| Untreated Control | 67.5 | 65 |
| 10 seconds | 25 | 49.5 |
| 1 minute | 52.5 | 50 |
| 2.5 minute | 52.5 | 42.5 |
| 5 minute | 20 | 12.5 |
| DPA-treated (1 minute, 1500 ppm) | 35 | 25 |

The results in Table 3E demonstrates that use of the AOX formulation reduces both superficial scald and softening in fruit.

The effect of benzyladenine (BA) on superficial scald development and softening was also examined (BA formualtion). BA was applied at the concentration originally present in the full formulation of Example 1. The BA formulation did not comprises any hexanal, geraniol, geranyl acetate, coumaric acid, ascorbic acid, ascorbyl palmitate, α-tocopherol, or tocopherol acetate.

Ten ml of the concentrate was diluted to a liter to form the final solution. The solution also contained calcium chloride (1% w/v final) and surfactant (0.1% v/v, final). Two bushels of apples were dipped in 40 liters of solution for each time period and subjected to controlled atmosphere storage as defined above. Apples were brought out after 9 months of storage. Twenty apples, from each treatment were picked randomly from two independent sets, and left at room temperature for a week before evaluating for scald and softening. The results are presented in Table 3F.

TABLE 3F

The effect of BA formulation of the present invention on scald development in Cortland apples. The number of apples showing scald or softening is expressed as a percentage of the total number of apples evaluated. The values are the mean from two independent evaluations.

| Duration of Treatment | Superficial scald % | Softening % |
|---|---|---|
| Untreated Control | 67.5 | 65 |
| 10 seconds | 60 | 72.5 |
| 1 minute | 52.5 | 52.5 |
| 2.5 minute | 32.5 | 25 |
| 5 minute | 27.5 | 30 |
| DPA-treated (1 minute, 1500 ppm) | 35 | 25 |

The results from Table 3E demonstrate that Benzyladenine application is moderately effective in reducing superficial scald and softening Collectively, the results from Tables 3A–3E demonstrate that the composition of Example 1 are,effective at reducing or eliminating superficial scald in fruit and reducing softening in fruit. Furthermore, components of the composition of Example 1, including enzyme activity modulators (EAM formulation), antioxidants (AOX formulation), or benzyladenine (BA formualtion), in the absence of other components, exhibit activity in reducing or eliminating superficial scald and in reducing fruit softening.

EXAMPLE 3

Effect of Spraying Compositions According to the Present Invention onto Red Haven Peaches Firmness and Soluble Solids A formulation prepared according to Example 1, comprising solutions A, B and C, is prepared and sprayed onto two trees (about 4 L/tree) about one month before harvest (+composition). Two control trees are sprayed with a similar amount of a solution comprising absolute ethanol (5 mL/JL) and the detergent ABG 7047 (Sylgard 309, Dow Corning may also be used), 1 mL/L (sprayed control), and two unsprayed trees are used as controls (unsprayed controls). All trees are of about the same age and all possessed the same root stocks. Peaches are harvested and quality parameters are analysed about 24 hours and one week post harvest. The results are described in Table 4.

TABLE 4

Quality Parameters of Fruit after Spraying with a Composition (Comp) of the Present Invention. Samples were determined 1 day and 7 days post harvest.

| Quality Parameter | 1 Day Post Harvest | | 7 Days Post Harvest | |
|---|---|---|---|---|
|  | Sample 1 | Sample 2 | Sample 1 | Sample 2 |
| Firmness (kg) | | | | |
| Unsprayed control | 5.07 ± 0.40 | 4.11 ± 0.13 | 3.05 ± 0.19 | 2.98 ± 0.11 |
| Sprayed control | 6.20 ± 0.48 | 6.38 ± 0.37 | 3.52 ± 0.14 | 4.25 ± 0.21 |
| Sprayed + comp | 6.00 ± 0.19 | 7.50 ± 0.27 | 3.42 ± 0.16 | 3.40 ± 0.25 |
| Soluble Solids* (%) | | | | |
| Unsprayed control | 9.31 ± 0.22 | 9.57 ± 0.28 | 9.71 ± 0.22 | 9.72 ± 0.22 |
| Sprayed control | 9.14 ± 0.25 | 8.98 ± 0.32 | 10.30 ± 0.22 | 10.00 ± 0.15 |
| Sprayed + comp | 9.70 ± 0.33 | 10.1 ± 0.19 | 10.28 ± 0.48 | 11.85 ± 0.25 |
| Fruit Weight (kg; avg of 15) | | | | |
| Unsprayed control | 1.66 | 1.86 | — | — |
| Sprayed control | 1.68 | 1.69 | — | — |
| Sprayed + comp | 2.32 | 2.35 | — | — |

*Soluble solids were estimated by monitoring the refractive index of the produce with a hand-held refractometer as would be evident to someone of skill in the art. However, other methods known in the art may be employed to measure soluble solids as would be evident to someone of skill in the art.

As shown in Table 4, the composition of the present invention enhances firmness, maintains soluble solids, and maintains or increases the average weight of produce suggesting that the compositions of the present invention are effective at preserving fruits, vegetables and other produce.

Colour Development

The effect of the compositions of the present invention was further assessed on the colour development of red haven peaches. A batch of ten peach trees were randomly selected and sprayed with the composition of the present invention (Example 1), the same number of trees were left untreated as control. Peaches were harvested at optimum ripeness and examined for colour development after five days. The peaches were stored at a temperature of 25° C. for full ripening. The colour values of 15 randomly selected peaches from each tree (10 control, 10 sprayed) were estimated, varying from 0 (no or very little colour) to a maximum of 8. The formulation was sprayed twice (2–4 L/tree depending on size) one month and fifteen days before harvest. The summary of the results is shown in Table 5.

TABLE 5

Peach Colour Values.

|  | Control Trees | Composition Applied to Trees |
|---|---|---|
| Mean of treatments | 2.47 ± 0.15 | 3.95 ± 0.4 |

The results shown in Table 5 indicate that the composition of the present invention enhances and maintains colour development in peaches.

EXAMPLE 4

Effects of the Composition of the Present Invention on Cherries

Hedel Cherries

The formulation of the present invention, prepared according to the method outlined in Example 1, comprising 1% (w/v) calcium chloride and 0.1% (v/v) surfactant were applied to one side of a cherry tree (4 L per side), the other side was left as a control. Four separate Hedel Cherry trees were sprayed. Cherries were harvested 2 weeks after spraying. The results are shown in Table 6 below.

TABLE 6

Quality Parameters of Hedel Cherries after Spraying with a Composition of the Present Invention

|  | Firmness (kg) | | Soluble Solids* (%) | |
|---|---|---|---|---|
| Tree # | Unsprayed side | Sprayed Side | Unsprayed side | Sprayed Side |
| 1 | 2.29 | 2.94 | 15 | 15.2 |
| 2 | 2.95 | 3.58 | 15 | 15.5 |
| 3 | 2.54 | 2.88 | 14.8 | 16.4 |
| 4 | 3.03 | 3.06 | 16.4 | 16 |

*Soluble solids were estimated by monitoring the refractive index of the produce with a hand-held refractometer.

The results shown in Table 6 demonstrate that the compositions of the present invention may be employed to enhance the quality of cherries.

The colour intensity of cherries was also determined in sprayed and unsprayed cherries. Samples were extracted in 95% ethanol over night, and the intensity of extracted colour determined at 500 nm. An increase in the OD was observed in ethanol extracts obtained from cherries that had been sprayed (OD 0.64 and 0.77 control, to 0.69 and 0.82 treated, respectively).

In alternate tests, the composition of the present invention was applied to cherry trees as described above. Cherries were harvested from the unsprayed and sprayed half of the trees. All the cherries within an equal segment were harvested irrespective of their conditions and separated into good, damaged and dry groups. "Damaged" was characterized by excessive softening, splitting or fungal infection. The results are shown in Table 7.

TABLE 7

Additional Quality Parameters of Hedel Cherries After Spraying with the Composition of the Present Invention (Fwt: Fresh weight).

|  | Unsprayed Cherries (Fwt kg) | | | Sprayed Cherries (Fwt kg) | | |
|---|---|---|---|---|---|---|
| Tree | Good | Damaged | Dry | Good | Damaged | Dry |
| 1 | 6.85 | 1.3 | 0.11 | 7.26 | 2.03 | 0.14 |
| 2 | 6.19 | 2.03 | 0.12 | 7.64 | 2.02 | 0.19 |
| 3 | 4.58 | 4.03 | 0.41 | 5.42 | 2.86 | 0.27 |
| 4 | 4.3 | 3.34 | 0.77 | 6.15 | 2.76 | 0.26 |
| Avg. | 21.92 | 10.7 | 1.41 | 26.47 | 9.67 | 0.86 |

The results shown in Table 7 indicate that the composition of the present invention protects and enhances the quality of cherries.

Vista Cherries

A modified formulation comprising hexanal, geraniol geranyl acetate, benzyl adenine, ascorbate and $\alpha$-tocopherol, 1% (w/v) calcium chloride and 0.1% (v/v) surfactant (ABG 7045; or Sylgard 309, Dow Corning) was prepared according to the method outlined in Example 1. The modified formulation did not comprise coumaric acid, ascorbyl palmitate and tocopherol acetate. The modified formulation was applied to one side of a cherry tree (4 L per side), the other side was left as a control. The spray treatment was repeated at least two weeks prior to harvest. Three separate Vista Cherry trees were sprayed. Cherries were harvested 2 weeks after spraying and stored at 4° C. in air. Quality of the cherries was evaluated every 2 weeks for an 8 week period. The results (mean of 20 independent samples, three estimations per sample) are shown in Table 8.

TABLE 8

Quality Parameters of Vista Cherries after Spraying with a Composition of the Present Invention

|  | Firmness (kg) | | Soluble Solids (%) | |
|---|---|---|---|---|
| Tree # | Unsprayed side | Sprayed Side | Unsprayed side | Sprayed Side |
| Initial properties | | | | |
| 1 | 1.89 | 1.89 | 19.8 | 20.4 |
| 2 | 1.61 | 1.64 | 19.6 | 16 |
| 3 | 1.67 | 1.9 | 19.2 | 19.2 |
| After Two weeks | | | | |
| 1 | 1.18 | 1.21 | 16.93 | 17.43 |
| 2 | 1.23 | 1.25 | 15.5 | 14.8 |
| 3 | 1.24 | 1.26 | 16.66 | 17.8 |
| After Four weeks | | | | |
| 1 | 1.25 | 1.34 | 16.37 | 16.6 |
| 2 | 1.14 | 1.24 | 15.4 | 15.08 |
| 3 | 1.08 | 1.29 | 15.97 | 16.1 |

TABLE 8-continued

Quality Parameters of Vista Cherries after Spraying
with a Composition of the Present Invention

| | Firmness (kg) | | Soluble Solids (%) | |
|---|---|---|---|---|
| Tree # | Unsprayed side | Sprayed Side | Unsprayed side | Sprayed Side |
| After Six weeks | | | | |
| 1 | 1.18 | 1.35 | 16.6 | 17 |
| 2 | 1.17 | 1.23 | 15.6 | 16 |
| 3 | 1.28 | 1.48 | 16.23 | 16.13 |

The results shown in Table 8 demonstrate that modified compositions of the present invention may be employed to enhance the quality of cherries.

Effect Individual Compounds of the Compositions of the Present Invention

Vista cherries were dipped in the antioxidant formulation as described above, as separate compound of the composition of the present invention, to evaluate the effects of individual components on shelf life and quality. The samples were dipped for 2.5 min in various components made into an aqueous solution containing 0.1% surfactant (ABG 7045; Sylgard 309, Dow Corning may also be used), ethanol (10 ml/l) and the required amount of the component(s). Samples were allowed to dry at room temperature and stored at 4° C. in air. Evaluations were conducted two weeks and four weeks after treatment. The results given are mean of twenty sample values. The results are shown in Table 9.

TABLE 9

Effect of postharvest dips of various compositions,
or individual components of the compositions
as described herein on Vista cherries.

| | Firmness (kg) | | Soluble Solids (%) | |
|---|---|---|---|---|
| Treatment | 2 weeks | 4 weeks | 2 weeks | 4 weeks |
| Full Composition[a] | 1.13 | 1.12 | 17.2 | 16.8 |
| Composition 1* | 1.25 | 1.16 | 16.2 | 16.8 |
| Composition 2** | 1.09 | 1.06 | 16 | 15.4 |
| Control: Ethanol (10 ml/l) | 1.21 | 1.02 | 15.8 | 15 |
| Hexanal (1 ml/l) | 1.24 | 1.16 | 16.4 | 15.8 |
| Geraniol (1 ml/l) | 1.01 | 1.24 | 16.8 | 17 |
| Geranyl Acetate (1 ml/l) | 1.21 | 1.12 | 17 | 14.6 |
| BA (200 mg/l) | 1.24 | 1.14 | 13.8 | 16.4 |
| CaCl$_2$ (10 g/l) | 1.26 | 1.09 | 16 | 15 |
| Ascorbic Acid (1 g/l) | 1.2 | 1.12 | 16.4 | 15 |
| α-tocopherol (1 ml · l) | 1.21 | 1.12 | 16.1 | 16.7 |

[a]composition as outlined in Example 1
*contains: Geraniol, Geranyl Acetate, Hexanal, BA, CaCl$_2$
**contains: Ascorbic acid, α-tocopherol, CaCl$_2$ These results indicate that geraniol, geranyl acetate, hexanal, CaCl$_2$ and BA result in increased firmness when applied to Vista cherries either alone or in combination. Geraniol, geranyl acetate, hexanal and α-tocopherol result in an increase in soluble solids. Furthermore, compositions comprising geraniol, geranyl acetate, hexanal, BA and CaCl$_2$ exhibit good firmness and soluble solids properties when applied to Vista cherries.

Bing Cherries

The composition as described in Example 1, comprising hexanal, geraniol geranyl acetate, benzyl adenine, ascorbate and α-tocopherol, 1% (w/v) calcium chloride and 0.1% (v/v) surfactant was prepared and applied as a pre-harvest spray to one side of a cherry tree (4 L per side), the other side was left as a control. The spray treatment was repeated at least two weeks prior to harvest. Three separate Bing Cherry trees were sprayed. Cherries were harvested 2 weeks after spraying and stored at 4° C. in air. Quality of the cherries was evaluated every 2 weeks for an 8 week period. The results (mean of 20 independent samples, three estimations per sample) are shown in Table 10.

TABLE 10

Quality Parameters of Bing Cherries after Spraying
with a Composition of the Present Invention

| | Firmness (kg) | | Soluble Solids (%) | |
|---|---|---|---|---|
| Tree # | Unsprayed side | Sprayed Side | Unsprayed side | Sprayed Side |
| Initial properties | | | | |
| 1 | 2.26 | 2.38 | 17 | 18.4 |
| 2 | 2.33 | 2.38 | 18.6 | 17.4 |
| 3 | 2.15 | 2.18 | 17.2 | 18.8 |
| After Two weeks | | | | |
| 1 | 2.2 | 2.16 | 19.4 | 19 |
| 2 | 1.94 | 1.97 | 17.8 | 19 |
| 3 | 1.88 | 1.92 | 17.6 | 18.2 |
| After Four weeks | | | | |
| 1 | 1.65 | 1.83 | 18.4 | 19.03 |
| 2 | 1.76 | 1.9 | 18.43 | 18.87 |
| 3 | 171 | 1.76 | 18 | 18.6 |
| After Six weeks | | | | |
| 1 | 2.26 | 2.54 | 17 | 18 |
| 2 | 2.47 | 2.79 | 17.27 | 18.27 |
| 3 | 2.27 | 2.29 | 17.33 | 17.87 |

The results shown in Table 10 further demonstrate that compositions of the present invention may be employed to enhance the quality of cherries.

EXAMPLE 5

Effects of the Composition of the Present Invention on Grapes

The effect of the composition of the present invention was assessed on grapes. Pinot Noir and Merlot grape vines were sprayed with the formulation of Example 1, comprising 1% calcium chloride and 0.1% (v/v) surfactant twice (two months and one month) prior to harvest. All bunches from unsprayed and sprayed vines were harvested. The results are shown in Table1.

TABLE 11

Effect of the Composition of the Present Invention on Grapes

| Characteristic Measured | Control | Composition applied |
|---|---|---|
| Number of vines | 5 | 4 |
| Number of bunches | 91 | 74 |
| Total weight (g) | 2922.7 | 4627.44 |
| Average weight per bunch (g) | 32.12 | 62.53 |

The results shown in Table 11 show that application of the formulationof the present invention to grapes significantly increases the yield weight of the grapes compared to grapes that are not treated with the formulation of the present invention. In addition to enhanced yield of the grapes, the treated grapes exhibited a better colour and appeared to be of a better quality than grapes that were not treated with the composition of the present invention.

EXAMPLE 6

Effects of the Composition of the Present Invention on Plums

Two varieties of blue plums, "Valerie" and "Valour" were sprayed with the composition. Alternate trees were assigned as control and for spray treatment within the same row. The variety "Valerie" received only one spray, as it was close to ripening. "Valour" received two sprays of the formulation, one month and 15 days before harvest. Fruits were harvested at optimum ripeness and stored at 4° C. in air. The data are the mean values of measurements from 10 plums from each tree, with three unsprayed control trees and four trees sprayed with the formulation. The data are presented in Tables 12A and 12B

TABLE 12A

Quality Parameters of Valeire plums after Spraying with a Composition of the Present Invention. The average weight of control plums was 848.67 g while that of sprayed plums was 846.50 g.

| | Firmness (kg) | | Soluble Solids (%) | |
|---|---|---|---|---|
| Time | Unsprayed side | Sprayed Side | Unsprayed side | Sprayed Side |
| Initial | 2.41 | 2.51 | 14.67 | 14.25 |
| 2 wks | 1.75 | 1.89 | 15.9 | 15.25 |
| 4 wks | 1.96 | 1.89 | 14.73 | 14.6 |
| 6 wks | 1.27 | 1.37 | 15.6 | 15.4 |
| 8 wks | 0.67 | 0.9 | 14.5 | 15.9 |

TABLE 12B

Quality Parameters of Valour plums after Spraying with a Composition of the Present Invention. The average weight of control plums was 609.33 g while that of sprayed plums was 675.67 g.

| | Firmness (kg) | | Soluble Solids (%) | |
|---|---|---|---|---|
| Time | Unsprayed side | Sprayed Side | Unsprayed side | Sprayed Side |
| Initial | 2.8 | 3.18 | 24.13 | 20.53 |
| 2 wks | 3.12 | 3.37 | 23.93 | 21.87 |
| 4 wks | 2.02 | 2.03 | 24.13 | 21.53 |

These results demonstrate that firmness is improved with pre-harvest application of the compositions of the present invention.

EXAMPLE 7

Phospholipase D Enzyme Assay

Phospholipase D (PLD) activity may be determined as described by Pinhero et al., 1998 by measuring the release of radiolabeled choline from 1,2-dipalmitoyl-$L_3$-phosphatidyl (N-methyl-$^3$H)choline at 23° C. The basic assay mixture contains 0.1M Tris-HCl (pH 7.5), 0.2 mM EGTA, membrane or cytosol protein (2.5 mg) and about 100,000 dpm of choline-labelled phosphatidylcholine in 0.1% (v/v) Triton X-100 (0.01% final), to make a total volume of 1 mL. To study the regulation of PLD by various compounds, the compound is added to the basic reaction mixture. The reaction is terminated after 10 min by adding 100 mL of 4N HCl followed by 1 mL of chloroform/methanol (2:1, v/v) and left overnight. The amount of [$^3$H]choline released during the reaction is determined by mixing a 0.5 mL aliquot of the aqueous phase directly into 5 mL of scintillation fluid (Ecolume, ICN) and determining the amount of radiolabel using a Beckman LS 6800 Scintillation counter (Beckman Instruments).

Estimation of PLD activity by monitoring the liberation of choline is a convenient and rapid method, but may be performed using other methods known in the art, for example, but not limited to, estimating PLD activity using fluorescent substrates or by estimating the amount of phosphatidylethanol formed (Harris et al., 1995; Pinhero et al., 1998).

EXAMPLE 8

Effects of the Composition of the Present Invention on Cut Flowers

The effect of the antioxidant composition of the present invention was assessed on cut flowers. Miniature white carnation flowers at stage 1 (tight bud stage) were divided into three groups of forty. One group was kept as control, another control group was sprayed with a solution containing 0.1 mL absolute ethanol and 0.1 mL ABG 7045 (Sylgard 309, Dow Coming may also be used). The third group was sprayed with a solution comprising 0.025 mL of the AOX formulation concentrate (Example 1, Solution B) and 0.1 mL ABG 7045 in 200 mL distilled water. The flowers were incubated at room temperature under normal illumination for ten days. The results are shown in Table 13.

TABLE 13

Effect of the Composition of the Present Invention on Cut Flowers

| | Numbers of flowers | |
|---|---|---|
| Stage of development | Control | Composition applied |
| Stage 1 | 0 | 0 |
| Stage 2 | 1 | 15 |
| Stage 3 | 12 | 25 |
| Stage 4 | 8 | 0 |
| Stage 5 | 18 | 0 |

Stage 1 - tight bud;
Stage 2 - partially open with yellow-tinted centre;
Stage 3 - fully open white flowers;
Stage 4 - petals show withering at the tip;
Stage 5 - fully withered flowers As there was no difference in the pattern of senescence between the unsprayed and sprayed controls, only the sprayed control is shown in Table 13. The results shown in Table 13 show that application of the AOX formulation of the present invention to cut flowers significantly decreases the senescence, therefore increasing the shelf life, of the flowers compared to flowers that are not treated with the formulation of the present invention.

All references are herein incorporated by reference.

REFERENCES

Anet, E. F. L. G., and Coggiola, I. M. (1974) J. Sci. Food Agr. 25, 293–298.

Barden, C. L. and Bramlage, W. J. (1994) Journal of Amer. Soc. Hort. Sci. 119, 264–269.

Blanpeid, G. D., Bramlage, W. J., Chu, C. L., Ingle, M., Kushad, M. M., Lau, O. L., and Lister, P. D. (1991) Can. J. of Plant Sci. 71, 605–608.

Ghahramani, F., Scott, K. J., Buckle, K. A. and Paton, J. E. (1999) J. Hortic. Sci. & Biotech. 74, 87–93.

Harris, W. E., Knutson, C. M., and Stahl, W. L. (1995) Plant Physiol. Biochem. 33, 389–398.

Patterson, M. E., and Workman M. (1962) Proc. Amer. Soc. Hortic. Sci. 90, 130–136.

Pierson, C. F. and Schomer, H. A. (1969) Hort Science 3,10.

Pinhero, R. G., Paliyath, G., Yada, R. Y., Murr, D. P. (1998) Plant. Physiol. Biochem. 36, 213–224.

The invention claimed is:

1. A composition for the preservation of produces, said composition comprising:
    a) at least one phospholipase D inhibitor from about 5.0 to about 5,000 µM;
    b) at least one compound comprising an isoprene subunit from about 5.0 to about 5,000 M; and
    c) at least one compound of the flavonoid biosynthetic pathway from about 5.0 to about 5,000 µM,
in a suitable medium.

2. The composition of claim 1, wherein said phospholipase D inhibitor is selected from the group consisting of hexanal, hexenol, hexenal, geraniol, and a combination thereof.

3. The composition of claim 1, wherein said compound comprising an isoprene subunit is selected from the group consisting of geraniol, geranylacetate, neral, nerol, citronellal, citronellol, and a combination thereof.

4. The composition of claim 1, wherein said component of the flavonoid biosynthetic pathway is selected from the group consisting of para-coumaric acid, trans-cinnamic acid, caffeic acid, and a combination thereof.

5. The composition of claim 1, further comprising at least one plant growth regulator, wherein said growth regulator is a cytokinin.

6. The composition of claim 1, wherein said suitable medium comprises ethanol methanol, water, or a combination thereof.

7. The composition of claim 6, wherein said suitable medium comprises water and ethanol.

8. The composition of claim 1, wherein said produce comprises processed produce, unprocessed produce, or partially processed produce.

9. The composition of claim 8, wherein said produce comprises fruit, vegetables or a combination thereof.

10. The composition of claim 1, further comprising an antioxidant, a membrane/cell wall stabilizing agent, a surfactant, or a combination thereof.

11. The composition of claim 10, wherein said antioxidant is selected from the group consisting of ascorbic acid, ascorbyl palmitate, α-tocopherol, α-tocopherol acetate, and a combination thereof.

12. The composition of claim 10, wherein said membrane/cell wall stabilizing agent is calcium chloride.

13. The composition of claim 10, wherein said surfactant comprises a food grade surfactant.

14. A method for preventing sunscald in produce comprising, applying an effective amount of the composition of claim 10 to said produce.

15. A method for preventing superficial scald in produce comprising, applying an effective amount of said composition of claim 10 to said produce.

16. A method for enhancing anthocyanin level in fruit comprising, applying an effective amount of said composition of claim 10 to said fruit.

17. The method of claim 16, wherein said fruit is selected from the group consisting of apples, peaches, nectarines, grapes, cherries, apricots, plums, prunes pears, berry crops, and citrus fruit.

18. A method for enhancing firmness, sweetness, shelf life, fruit quality or a combination thereof in fruit comprising, applying an effective amount of said composition of claim 10 to said fruit.

19. The method of claim 18, wherein said fruit is selected from the group consisting of apples, peaches, nectarines, grapes, cherries, apricots, plums, prunes pears, berry crops, and citrus fruit.

20. A method for enhancing the levels of proteins and isoflavonoids in soybean, comprising, applying an effective amount of the composition of claim 10 to said soybean.

21. A method for enhancing the sugar level of beets or sugar cane comprising, applying an effective amount of the composition of claim 10 to said beets or sugar cane.

22. A method for enhancing shelf life of cut flowers, comprising, applying an effective amount of the composition of claim 10 to said cut flowers.

23. A matrix coated or impregnated with the composition of claim 1.

24. A method for preserving produce comprising, applying an effective amount of said composition of claim 1 to said produce.

25. The method of claim 24, wherein said composition additionally comprises an antioxidant, a membrane stabilizing agent, a surfactant, or a combination thereof.

26. The method of claim 24, wherein applying comprises spraying.

27. The method of claim 26, wherein spraying comprises pre-harvest spraying.

28. The method of claim 24, wherein applying comprises dipping.

29. The method of claim 24, wherein applying comprises storage in a medium comprising said composition.

30. A composition for the preservation of produce comprising from about 5.0 to about 5,000 µM, geraniol, geranyl acetate from about 5.0 to about 5,000 µM, hexanal and from about 5.0 to about 5,000 µM, coumaric acid in a suitable medium.

31. A method for preserving produce comprising, applying an effective amount of said composition of claim 30 to said produce.

32. A matrix coated or impregnated with the composition of claim 30.

33. A composition for the preservation of produce, said composition comprising:
    a) at least one phospholipase D inhibitor at a concentration from about 5.0 to about 5,000 M, and selected from the group consisting of hexanal, hexenol, hexenal, geraniol, and a combination thereof;
    b) at least one compound comprising an isoprene subunit at a concentration from about 5.0 to about 5,000 µM, and selected from the group consisting of geraniol, geranylacetate, neral, nerol, citronellal, citronellol, and a combination thereof;
    c) at least one component of the flavonoid biosynthetic pathway at a concentration from about 5.0 to about 5,000 µM, and selected from the group consisting of para-coumaric acid, trans-cinnamic acid, caffeic acid, and a combination thereof;
    d) at least one plant growth regulator, wherein said growth regulator is a cytokinin;
    e) an antioxidant selected from the group consisting of ascorbic acid, ascorbyl palmitate, α-tocopherol, α-tocopherol acetate, and a combination thereof;
    f) $CaCl_2$; and
    g) a surfactant, in a suitable medium comprising ethanol, methanol, water, or a combination thereof.

* * * * *

UNITED STATES PATENT AND TRADEMARK OFFICE
CERTIFICATE OF CORRECTION

PATENT NO.       : 7,198,811 B2                                              Page 1 of 1
APPLICATION NO.  : 10/884864
DATED            : April 3, 2007
INVENTOR(S)      : Paliyath et al.

It is certified that error appears in the above-identified patent and that said Letters Patent is hereby corrected as shown below:

In column 25, line 11, in Claim 1, delete "produces," and insert -- produce, --, therefor.

In column 25, line 16, in Claim 1, delete "5,000 M;" and insert -- 5,000 µM; --, therefor.

In column 25, line 36, in Claim 6, after "ethanol" insert -- , --.

In column 25, line 66, in Claim 17, after "prunes" insert -- , --.

In column 26, line 7, in Claim 19, after "prunes" insert -- , --.

In column 26, line 14, in Claim 22, after "flowers" delete ",".

In column 26, line 45, in Claim 33, delete "5,000 M," and insert -- 5,000 µm, --, therefor.

Signed and Sealed this

Thirteenth Day of November, 2007

JON W. DUDAS
*Director of the United States Patent and Trademark Office*